United States Patent [19]

Park

[11] Patent Number: 5,536,494
[45] Date of Patent: Jul. 16, 1996

[54] POLYETHYLENE OXIDE-CONTAINING QUATERNARY AMMUNIUM POLYMERS AND PHARMACEUTICAL COMPOSITIONS CONTAINING AN ANTIMICROBIAL AMOUNT OF SAME

[75] Inventor: Joonsup Park, Arlington, Tex.

[73] Assignee: Alcon Laboratories, Inc., Fort Worth, Tex.

[21] Appl. No.: 318,022

[22] Filed: Oct. 4, 1994

[51] Int. Cl.$^6$ .......................... A61K 31/785; A61L 2/16
[52] U.S. Cl. .................. 424/78.04; 514/839; 514/840; 424/78.08
[58] Field of Search .................. 424/78.04; 528/422

[56] References Cited

U.S. PATENT DOCUMENTS

| | | | |
|---|---|---|---|
| 3,778,476 | 12/1973 | Rembaum et al. | 260/567.6 |
| 3,874,870 | 4/1975 | Green et al. | 71/67 |
| 3,898,336 | 8/1975 | Rembaum et al. | 424/25 |
| 3,931,319 | 1/1976 | Green et al. | 260/567.6 |
| 4,001,432 | 1/1977 | Green et al. | 424/329 |
| 4,012,446 | 3/1977 | Green et al. | 260/567.6 |
| 4,025,653 | 5/1977 | Green et al. | 424/325 |
| 4,026,945 | 5/1977 | Green et al. | 260/567.6 |
| 4,027,020 | 5/1977 | Green et al. | 424/248.56 |
| 4,036,959 | 7/1977 | Green et al. | 424/248.56 |
| 4,055,712 | 10/1977 | Green et al. | 526/11.1 |
| 4,089,977 | 5/1978 | Green et al. | 424/329 |
| 4,091,113 | 5/1978 | Green et al. | 424/329 |
| 4,150,115 | 4/1979 | Jacquet et al. | 528/397 |
| 4,250,269 | 2/1981 | Buckman et al. | 525/496 |
| 4,304,910 | 12/1981 | Green et al. | 544/87 |
| 4,407,791 | 10/1983 | Stark | 424/80 |
| 4,444,750 | 4/1984 | Green et al. | 424/70 |
| 4,474,751 | 10/1984 | Haslam et al. | 424/78.04 |
| 4,499,077 | 2/1985 | Stockel et al. | 424/149 |
| 4,525,346 | 6/1985 | Stark | 424/80 |
| 4,567,302 | 1/1986 | Sivaramakrishnan | 564/256 |
| 4,654,208 | 3/1987 | Stockel et al. | 424/78 |
| 4,970,211 | 11/1990 | Fenyes et al. | 514/252 |
| 5,037,647 | 8/1991 | Chowhan et al. | 424/78 |
| 5,277,901 | 1/1994 | Vigh et al. | 424/78.04 |
| 5,300,287 | 4/1994 | Park | 424/78.04 |

FOREIGN PATENT DOCUMENTS

| | | |
|---|---|---|
| 0115619A1 | 8/1984 | European Pat. Off. . |
| 0214850 | 3/1987 | European Pat. Off. . |
| 2518634A | 8/1993 | Germany . |
| 536017 | 4/1941 | United Kingdom . |
| 1513672 | 6/1978 | United Kingdom . |
| 1556365 | 11/1979 | United Kingdom . |
| WO91/09523 | 7/1991 | WIPO . |
| WO93/07251 | 4/1993 | WIPO . |
| WO93/12820 | 7/1993 | WIPO . |
| WO94/19943 | 9/1994 | WIPO . |

OTHER PUBLICATIONS

Devinsky et al., "Preparation of N,N'-bis(alkyldimethyl)-3-oxa 1,=5-pentanediammaoium dibromides as antimicrobiagents", No. 23322, *Chemical Abstracts*, vol. 110, 498–499 (199).

Keegstra et al., "a Highly Selective Synthesis of Monodisperse Oligo (ethylene glyuols)", *J. Org. Chem.*, 57:6678–680 (1992).

*Primary Examiner*—Peter F. Kulkosky
*Attorney, Agent, or Firm*—Patrick M. Ryan

[57] ABSTRACT

PEO-containing quaternary ammonium compounds have good broad spectrum antimicrobial activity. These compounds are useful in pharmaceutical compositions as preservatives and in contact lens care compositions as preservatives and/or disinfectants.

23 Claims, No Drawings

POLYETHYLENE OXIDE-CONTAINING QUATERNARY AMMUNIUM POLYMERS AND PHARMACEUTICAL COMPOSITIONS CONTAINING AN ANTIMICROBIAL AMOUNT OF SAME

BACKGROUND OF THE INVENTION

The present invention relates to a class of ionene polymeric compounds which are useful as antimicrobials in pharmaceutical and cosmetic compositions. In particular, the present invention relates to certain polyethylene oxide (PEO)-containing polymeric quaternary ammonium compounds. These compounds are useful as disinfectants and preservatives for pharmaceutical products, including ophthalmic compositions and contact lens care products.

It is well known that small organic compounds, such as benzalkonium chloride (BAC), chlorhexidine, thimerosal have excellent antimicrobial activity. These compounds have been commercially used as preservatives and disinfectants for many years; however, there are some significant disadvantages to using these compounds, especially in ophthalmic and contact lens compositions. In particular, it is now known that these small organic antimicrobials are often toxic to the sensitive tissues of the eye and can accumulate in contact lenses, particularly soft, hydrophilic contact lenses. Accumulation of these antimicrobial compounds in contact lenses may cause eye irritation, and leaching of such compounds may occur while the lens is in the eye, causing further irritation and possibly damaging the cornea.

Several classes of polymeric antimicrobials were subsequently developed to overcome the disadvantages of the above-described monomeric compounds. These polymeric antimicrobials had lower cytotoxicity and had minimal interaction with biomaterials. Such antimicrobials include those described in U.S. Pat. Nos. 3,931,319; 4,001,432; 4,012,446; and 4,836,986.

U.S. Pat. No. 5,277,901 discloses certain antimicrobial PEO-containing quaternary ammonium polymers as useful for ophthalmic compositions, such as contact lens cam compositions, when combined with at least one other antimicrobial agent. The additional antimicrobial agent is preferably an urea component.

SUMMARY OF THE INVENTION

For purposes of this specification, disinfectants and/or preservatives shall be collectively referred to as "antimicrobials" and compounds having disinfecting and/or preserving efficacy shall be referred to as compounds having "antimicrobial activity."

It has now surprisingly been found that PEO-containing quaternary ammonium polymers comprising a repeating unit of the formula

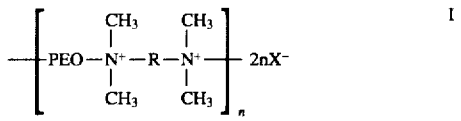

wherein:

R=polyethylene oxide of molecular weight from 80–2,000; CH$_2$-phenyl-CH$_2$; or 2-butenyl;

PEO=polyethylene oxide of molecular weight from 80–2,000;

X=halogen, acetate, or sulfate; and n=5–100;

exhibit excellent antimicrobial activity.

The ophthalmic compositions of the present invention comprise the PEO-containing quaternary ammonium polymers of the present invention. These compositions include: contact lens care products, such as chemical disinfecting and storage solutions and preserved saline solutions; and other types of ophthalmic compositions, such as artificial tears and topical pharmaceutical preparations.

DETAILED DESCRIPTION OF THE INVENTION

The polymers of the present invention comprise a repeating unit represented by the following general formula:

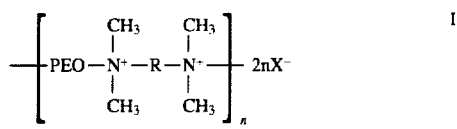

wherein:

R=polyethylene oxide of molecular weight from 80–2,000; CH$_2$-phenyl-CH$_2$; or 2-butenyl;

PEO=polyethylene oxide of molecular weight from 80–2,000;

X=halogen, acetate, or sulfate; and n=5–100.

In the case where R is chosen to be polyethylene oxide of molecular weight from 80–2,000, R may be the same or different than the PEO group shown in formula I.

The preferred compounds of formula I are those wherein:

PEO=polyethylene oxide of molecular weight from 80–1,000;

X=Cl; and n=10–70.

Most preferred are the compounds of formula I wherein:

R=2-butenyl;

PEO=polyethylene oxide of molecular weight from 80–500;

X=Cl; and n=20–40.

In one of the preferred embodiments, the PEO in the compounds of formula I has a molecular weight of about 400 and the compounds have a number average molecular weight (based on NMR spectrum) of at least 5000.

The end groups on each end of the polymers of formula I may be, but do not have to be, the same. Two preferred end groups for the compounds of formula I are N(CH$_3$)$_2$ and OCH$_2$CH$_2$Cl.

Without wishing to be bound to any theory, it is believed that the compounds of the present invention possess a lower quaternary ammonium salt ("quat") charge density than currently available antimicrobial polymeric quat compounds. One hypothesis is that the intramolecular interactions between the oxygen in the PEO and the quat may result in a reduction in the charge density on the quat. In turn, it is believed that a lower quat charge density decreases interactions with, for example, charged contact lens materials such as those categorized as "Group IV" by the FDA. Decreased interactions between the quat-containing polymer and the lens material would result in less accumulation of the polymer on the contact lens, and consequently less irritation and/or other toxic side effects.

The PEO useful in forming the compounds of the present invention is commercially available from a variety of sources, including Aldrich Chemical Company (Milwaukee, Wis.). The PEO from these sources is typically available as a mixture of PEO compounds of various molecular weights and is characterized by an average molecular weight. Also included within the scope of the present invention, however, is the use of PEO having a defined molecular weight such that each PEO compound has the same molecular weight.

PEO having a defined molecular weight corresponding to two PEO units is commercially available from Aldrich Chemical Company. The 2-unit PEO is available as Cl—$CH_2$—$CH_2$—O—$CH_2$—$CH_2$—Cl. The 4-and 6-unit PEOs are also available from Aldrich Chemical Company, but with —OH instead of —Cl end groups. Higher defined molecular weight PEO, up to molecular weights corresponding to about 20 PEO units, can be made by known methods, such as that described by Keegstra, et. al., J. Org. Chem., 57:6678 (1992).

The PEO starting material should be in dihalide form, and if not already in such form, is first converted to a dihalide form by known methods. For example, the —OH end groups of PEO can be converted to the corresponding dihalide PEO by reaction with either thionyl chloride or thionyl bromide in the presence of pyridine.

The compounds of formula I (R=polyethylene oxide of molecular weight from 80–2,000; $CH_2$-phenyl-$CH_2$; or 2-butenyl) can be made by the following procedure. The dihalide PEO is reacted with a diamine monomer, such as N,N,N',N'-tetramethyl-1,4-diamino-2-butene either in the presence of a solvent, such as dimethylsulfoxide, or in the absence of a solvent. The solvent is necessary for those low (approximately 500 or less) molecular weight dihalide PEO compounds which become difficult to stir as the reaction progresses. If the halide in the dihalide PEO is Cl, the reaction is carried out at approximately 130° C. for 4–5 hrs. If the halide is Br, the reaction can be carried out under milder conditions, and temperatures around 85° C. are suitable in most instances. After the reaction of the dihalide PEO with the diamine monomer, the resulting polymer is purified by a precipitation method.

Alternatively, the compounds of formula I where R=$CH_2$-phenyl-$CH_2$ or 2-butenyl can be synthesized by the following preferred procedure. The dihalide PEO is reacted with an excess amount of N,N-dimethylamine in a pressure bottle. The resulting product is then reacted with either 1,4-dichloro-2-butene at about 70° C. to produce the compound of formula I (R=2-butenyl), or with p-xylene,α,α-dihalide at about 80°–85° C. for about 5 hrs. to produce the compound of formula I (R=$CH_2$-phenyl-$CH_2$).

The following examples are offered for illustrative purposes only and in no way are intended to restrict or limit the present invention.

The following compounds were prepared:

| EX-AM-PLE | PEO MW | R | INITIAL REACTANT MOLAR FEED RATIO PEO:AMINE | COMPOUND OF FORMULA 1 MW (number avg.) |
|---|---|---|---|---|
| 1 | 200 (avg.) | 2-butenyl | 1:1 | N.D. |
| 2 | 400 (avg.) | 2-butenyl | 1:1 | 6110 |
| 3 | 400 (avg.) | 2-butenyl | 0.75:1 | 3050 |
| 4 | 400 (avg.) | 2-butenyl | 0.5:1 | 1710 |
| 5 | 106 | 2-butenyl | 1:1 | N.D. |

N.D. = not determined

SYNTHESIS OF EXAMPLE 1

A mixture of 20 g. (0.1 mol) of polyethylene oxide (average molecular weight 200, Aldrich) and 15.8 g (0.2 mol) of pyridine in 300 ml of toluene was reacted with 25 g (0.21 mol) of thionyl chloride by dropwise addition. This mixture was reacted at 110° C. for 6 hrs. The toluene solvent was decanted and the sedimented solid material was washed with toluene (20 ml×1 ). The combined toluene solution was concentrated in vacuo and dissolved in chloroform (200 ml). The chloroform solution was washed with saturated sodium chloride solution (30 ml×2), dried over anhydrous sodium sulfate, and concentrated in vacuo to leave 20 g (84.7% yield) of dichloro-PEO monomer in the form of an oily material. A mixture of the above dichloro-PEO monomer (4.0 g, 0.017 mol) and N,N,N'N'-tetramethyl-1,4-diamino-2-butene (Aldrich) was reacted at 125° C. for 24 hrs. with a mechanical stirrer to give a viscous material. This viscous material was dissolved in ethanol and precipitated with ethyl acetate. This process was repeated 3 times and then the compound was dried in high vacuum. Elemental Analysis: Calcd. for $C_{17}H_{36}N_2Cl_2O_{4.5}.75H_2O$: C, 48,06;H, 8.90; N, 6.59 Found: C, 48.36; H, 9.38; N, 6.51.

SYNTHESIS OF EXAMPLE 2

The above procedure of forming a dichloro PEO monomer was repeated, except this time PEO with an average molecular weight of 400 (Aldrich) was used. The dichloro compound (4.36 g, 0.01 mol) was reacted with 1.42 g (0.01 mol) of N,N,N',N'-tetramethyl-1,4-diamino-2-butene in dry DMSO solvent and the mixture was reacted at 120° C. for 3 hrs. and precipitated with ethyl acetate. The precipitate was dissolved in methanol and precipitated again with ethyl acetate. This process was repeated 3 times and dried in high vacuum. Number average molecular weight of the resulting compound was calculated to be about 6110 (based on NMR spectrum).

SYNTHESIS OF EXAMPLE 3

The same procedure described in Example 2 was used, except that a feed ratio of PEO: Amine of 0.75:1 was used. The resulting compound had a number average molecular weight (based on NMR Spectrum) of 3050.

SYNTHESIS OF EXAMPLE 4

The procedure of Example 2 was again followed except that a feed ratio of PEO: Amine of 0.51:1 was used. The resulting compound had a number average molecular weight (based on NMR spectrum) of 1710.

SYNTHESIS OF EXAMPLE 5

A mixture of 2-chloroethylether (7.15 g, 0.05 mol) and 7.1 g (0.05 mol) of N,N,N'N-tetramethyl-1,4-diamino-2-butene was reacted in to ml DMSO at 120° C. for 24 hrs. under the stream of argon gas. A yellow colored precipitate was formed. This mixture was treated with ethyl acetate to precipitate. This was dissolved in methanol and was precipitated again with ethyl acetate. This process was repeated 3 times and dried in high vacuum. Elemental Analysis: Calcd. for $C_{12}H_{26}N_2Cl_2.0.075H_2O(290.76)$: C, 48.24; H, 9.18; N, 9.37 Found: C, 48.38; H, 9.38; N, 9.00

The antimicrobial activity of the compounds of Examples 1–5 was evaluated as follows.

A stock culture of *Serratia marcescens* ATCC 14041 was subcultured onto soybean casein digest agar slants and incubated overnight at 30°–35° C. After 18–24 hours, the slants were rinsed with 0.9% sodium chloride solution and the suspension adjusted to contain 1×10⁸ CFU/mL viable cells.

Five test solutions were prepared, each consisting of 0.001% by weight of the respective exemplary compounds in purified water. Ten mL of each test solution were dispensed into sterile screw cap tubes, inoculated with 0.1 mL of either the bacterial or fungal suspension and vortexed. At selected time intervals, the tubes were vortexed, one mL samples removed, serially diluted and pour plates prepared. The plates were incubated for 48–72 hours and observed for the presence of surviving microorganisms.

The results are shown in Table 1.

TABLE 1

| Compound Example No. | Compound Conc. (wt %) | 0 | 1 HR | 2 HR | 4 HR | 24 HR | 48 HR | Day 7 | Day 14 |
|---|---|---|---|---|---|---|---|---|---|
| 1 | 0.001 | $3.9 \times 10^4$ | $1.7 \times 10^3$ | $8.9 \times 10^2$ | <10 | <10 | <10 | <10 | <10 |
| 2 | 0.001 | $1.1 \times 10^6$ | $1.0 \times 10^5$ | $5.8 \times 10^4$ | $1.7 \times 10^4$ | <10 | <10 | <10 | $1.1 \times 1.0^2$ |
| 3 | 0.001 | $1.1 \times 10^6$ | $2.2 \times 10^5$ | $1.9 \times 10^5$ | $1.2 \times 10^5$ | $2.5 \times 10^4$ | $7.8 \times 10^2$ | $5.0 \times 10^0$ | <10 |
| 4 | 0.001 | $1.1 \times 10^6$ | $5.5 \times 10^5$ | $4.0 \times 10^5$ | $3.5 \times 10^5$ | $2.2 \times 10^5$ | $11 \times 10^5$ | $1.3 \times 10^5$ | $6.7 \times 10^3$ |
| 5 | 0.001 | $7.7 \times 10^5$ | $2.5 \times 10^2$ | $8.7 \times 10^2$ | <10 | <10 | <10 | <10 | <10 |

The polymers of the present invention may be used as antimicrobials in ophthalmic compositions, particularly as disinfectants in contact lens care products and as preservatives in other types of ophthalmic compositions, such as artificial tears or topical pharmaceutical preparations. In general, the polymers of the present invention will be present in the compositions at a concentration from about 0.1 to about 0.0001 percent by weight (wt %). If used as either a disinfectant or a preservative, the polymers are preferably present at a concentration from about 0.05 to about 0.0005 wt %. Most preferred for both disinfectant and preservative applications is a polymer concentration of about 0.001 wt %.

The ophthalmic compositions of the present invention may additionally contain other components, for example, ophthalmically acceptable buffers, tonicity agents, surfactants and therapeutic agents.

EXAMPLE 6

Preserved Saline or Contact Lens Disinfecting Formulation

| Ingredient | w/v % |
|---|---|
| Compound of formula I | 0.001 |
| Sodium Citrate | 0.56 |
| Citric Acid | 0.021 |
| Sodium Chloride | 0.52 |
| EDTA | 0.05 |
| NaOH/HCl | pH 7 |
| Purified Water | q.s. |

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A pharmaceutical composition comprising an antimicrobially-effective amount of a polymer having a single repeating unit of the formula

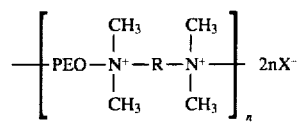

wherein

R=polyethylene oxide of molecular weight from 80–2,000; CH₂-phenyl-CH₂; or 2-butenyl;

PEO=polyethylene oxide of molecular weight from 80–2,000;

X=halogen, acetate, or sulfate; and n=5–100;

and a pharmaceutically acceptable carrier therefor.

2. The composition of claim 1, wherein the polymer is present at a concentration from about 0.1 to about 0.0001 wt %.

3. The composition of claim 2, wherein the polymer is present at a concentration from about 0.05 to about 0.0005 wt %.

4. The composition of claim 3, wherein the polymer is present at a concentration of about 0.001 wt %.

5. The composition of claim 1 wherein R=polyethylene oxide of molecular weight from 80–2,000.

6. The composition of claim 1 wherein R=CH₂-phenyl-CH₂.

7. The composition of claim 1 wherein R=2-butenyl.

8. The composition of claim 1 wherein PEO=polyethylene oxide of molecular weight from 80–1000; X=Cl; and n=10–70.

9. The composition of claim 8 wherein R=2-butenyl; PEO=polyethylene oxide of molecular weight from 80–500; and n=20–40.

10. The composition of claim 1, wherein the polymer has a number average molecular weight, based on NMR spectroscopy, of at least 5,000, has end groups independently selected from the group consisting of N(CH₃)₂ and OCH₂CH₂Cl, and wherein PEO=polyethylene oxide of molecular weight 400;

X=Cl; and n=10–70.

11. The composition of claim 10, wherein R=2-butenyl; and n=20–40.

12. A method of disinfecting a contact lens, comprising contacting, for a time sufficient to disinfect the lens, the contact lens to a composition comprising a disinfecting amount of a polymer having a single repeating unit of the formula

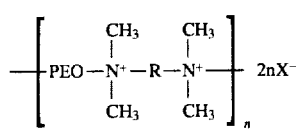

wherein

R=polyethylene oxide of molecular weight from 80–2,000; $CH_2$-phenyl-$CH_2$; or 2-butenyl;

PEO=polyethylene oxide of molecular weight from 80–2,000;

X=halogen, acetate, or sulfate; and n=5–100;

and a pharmaceutically acceptable carrier therefor.

13. The method of claim 12, wherein the compound of formula I is present at a concentration from about 0.1 to about 0.0001 wt %.

14. The method of claim 13, wherein the compound of formula I is present at a concentration from about 0.05 to about 0.0005 wt. %.

15. The method of claim 14, wherein the compound of formula I is present at a concentration of about 0.001 wt %.

16. The method of claim 12 wherein R=polyethylene oxide of molecular weight from 80–2,000.

17. The method of claim 12 wherein R=$CH_2$-phenyl-$CH_2$.

18. The method of claim 12 wherein R=2-butenyl.

19. The method of claim 12 wherein PEO=polyethylene oxide of molecular weight from 80–1000; X=Cl; and n=10–70.

20. The method of claim 19 wherein R=2-butenyl; PEO=polyethylene oxide of molecular weight from 80–500; and n=20–40.

21. The method of claim 12, wherein the polymer has a number average molecular weight, based on NMR spectroscopy, of at least 5,000, has end groups independently selected from the group consisting of $N(CH_3)_2$ and $OCH_2CH_2Cl$, and wherein PEO=polyethylene oxide of molecular weight 400;

X=Cl; and n=10–70.

22. The method of claim 21, wherein R=2-butenyl; and n=20–40.

23. A polymer comprising a single repeating unit of the formula

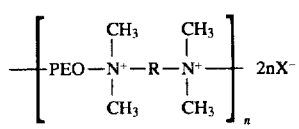

wherein

R=polyethylene oxide of molecular weight from 80–2,000; $CH_2$-phenyl-$CH_2$; or 2-butenyl;

PEO=polyethylene oxide of molecular weight from 80–2,000;

X=halogen, acetate, or sulfate; and n=5–100.

* * * * *